United States Patent
Nashef et al.

(10) Patent No.: US 7,156,868 B1
(45) Date of Patent: Jan. 2, 2007

(54) HEAT TRANSFER DEVICES

(75) Inventors: Aws Nashef, Glasgow (GB); Ted Vander Wiede, Strathaven (GB); Robert Macnair, Glasgow (GB); Stephen Wilson, Edinburgh (GB); Simon Andrews, Glasgow (GB)

(73) Assignee: Omega Critical Care Limited, Scotland (GB)

( * ) Notice: Subject to any disclaimer, the term of this patent is extended or adjusted under 35 U.S.C. 154(b) by 222 days.

(21) Appl. No.: 10/069,649

(22) PCT Filed: Aug. 25, 2000

(86) PCT No.: PCT/GB00/03273

§ 371 (c)(1),
(2), (4) Date: Sep. 13, 2002

(87) PCT Pub. No.: WO01/13808

PCT Pub. Date: Mar. 1, 2001

(30) Foreign Application Priority Data

Aug. 26, 1999 (GB) .................................. 9920112.1

(51) Int. Cl.
*A61F 7/12* (2006.01)
(52) U.S. Cl. ........................... 607/113; 604/113; 607/99
(58) Field of Classification Search ................ 600/595, 600/520, 526, 549, 561, 505; 606/24; 604/113; 607/99, 113
See application file for complete search history.

(56) References Cited

U.S. PATENT DOCUMENTS

| | | | | |
|---|---|---|---|---|
| 4,836,214 A | * | 6/1989 | Sramek | ...................... 600/506 |
| 5,037,395 A | * | 8/1991 | Spencer | ...................... 604/113 |
| 5,056,526 A | * | 10/1991 | Khalil | ......................... 600/505 |
| 5,247,136 A | | 9/1993 | Mitsuyasu et al. | |
| 5,364,357 A | | 11/1994 | Aase | |
| 5,380,320 A | * | 1/1995 | Morris | ......................... 606/33 |
| 5,474,080 A | * | 12/1995 | Hughes | ...................... 600/526 |
| 5,509,424 A | | 4/1996 | Al-Ali | |
| 5,634,470 A | * | 6/1997 | Norris | ......................... 600/526 |
| 5,682,899 A | * | 11/1997 | Nashef et al. | .............. 600/505 |
| 5,720,775 A | | 2/1998 | Larnard | |
| 5,727,553 A | * | 3/1998 | Saad | ........................... 600/407 |
| 5,857,976 A | * | 1/1999 | Quinn et al. | ................. 600/506 |
| 5,865,801 A | * | 2/1999 | Houser | ................... 604/103.07 |
| 5,921,924 A | | 7/1999 | Avitall | |
| 6,144,870 A | * | 11/2000 | Griffin, III | ................... 600/374 |
| 6,208,881 B1 | * | 3/2001 | Champeau | ................... 600/374 |
| 6,387,052 B1 | * | 5/2002 | Quinn et al. | ................. 600/505 |
| 6,400,976 B1 | * | 6/2002 | Champeau | ................... 600/374 |
| 6,562,030 B1 | * | 5/2003 | Abboud et al. | ............... 606/21 |
| 2001/0037812 A1 | * | 11/2001 | Dobak et al. | ............... 128/898 |

* cited by examiner

*Primary Examiner*—Roy D. Gibson
(74) *Attorney, Agent, or Firm*—Drinker Biddle & Reath LLP

(57) ABSTRACT

A catheter having a heat transfer device at or near its distal end, wherein the heat transfer device is layered or coated onto or into the catheter wall is described. The heat transfer device is preferably a flexible film having one or more electrical resistor flow paths thereon or therethrough, or is disposed directly onto the catheter wall by a deposition process. The heat transfer device may alternatively be formed by a length of the catheter wall being formed wholly, substantially of partly from doped material able to act as a heat transfer device upon application of power therethrough. The heat transfer device is preferably powered by one or more metal wires co-extruded within the catheter body.

17 Claims, 3 Drawing Sheets

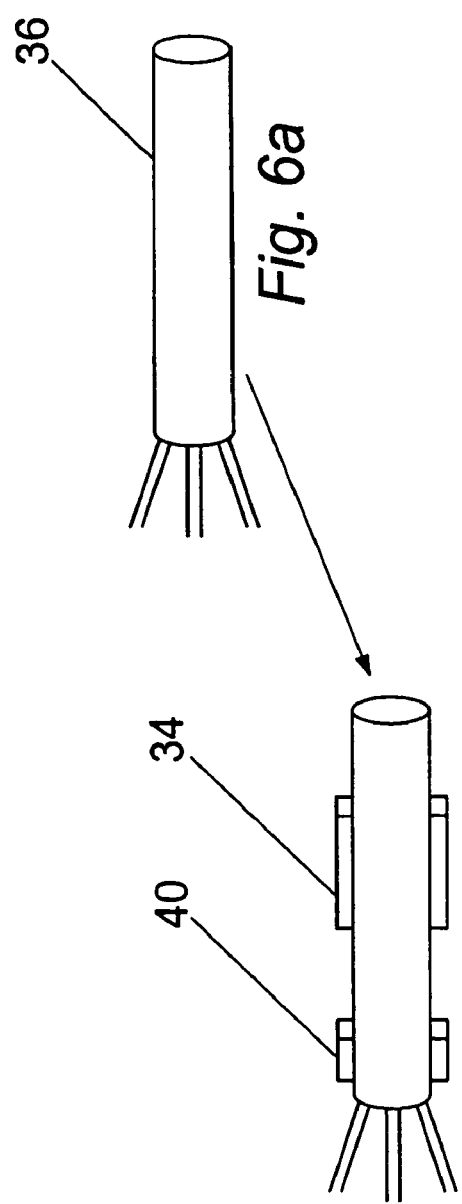
Fig. 6a
Fig. 6b
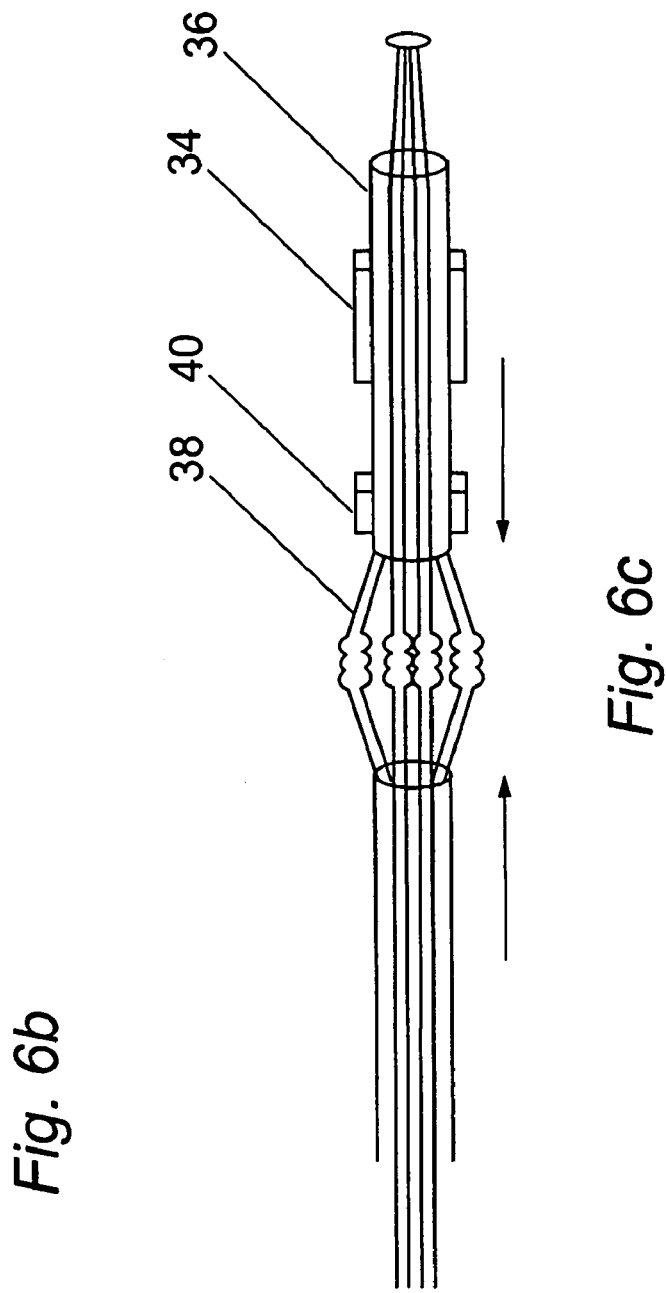
Fig. 6c

HEAT TRANSFER DEVICES

The present invention relates to improvements for catheters having a heat transfer device at or near their distal end.

One of the present constraints concerning manufacture of catheters designed to monitor various cardiac output data is the manner and form of the required heat transfer device system. One present form of heat transfer device involves a thermal coil radially disposed about the catheter body to form a generally tubular coil which extends along the outside wall of the catheter. Such a heat transfer device is shown in U.S. Pat. No. 5,509,424. However, such heat transfer coils require time and effort to wind and form and also restrict the possible miniaturisation of such catheters for use in paediatrics.

It is an object of the present invention to provide improvements to the manner and nature of heat transfer devices for use with catheters.

Thus, according to one aspect of the present invention, there is provided a catheter having a heat transfer device at or near its distal end, wherein the heat transfer device is layered or coated onto or into the catheter wall.

In one embodiment, the heat transfer device is a flexible film having one or more electrical resistor flow paths thereon or therethrough, which film is locatable around the catheter wall.

Such films can include flexible metal films on which one or more electrical paths have been etched or otherwise created. Alternatively, one or more electrical paths could be added onto a plastic film backing. The form of addition includes any type of deposition or coating, and the one or more electrical paths could be formed by etching, etc to form the resistor structure.

One or more temperature sensors or sensor leads could be included on or within the heat transfer device film to monitor the temperature of the electrical path(s), and thus the temperature of the overall heat transfer device.

Suitable backing materials include PVC, polyurethane, silk, synthetic silk, silicon rubber, Elaston™ etc, possibly about 20–80 microns thick, and suitable thin high resistant metal films include nickel, chromium or nickel-chromium. These can be deposited on the plastic backing material, and patterned using a photolithography mask to form the resistor structure.

On top of the resistor structure could be located a suitable insulator like parylene C, followed by deposition of a suitable temperature sensing means e.g. thermistors or platinum. Finally the outer surface may be coated with a silver or gold layer, possibly 5–10 microns thick. This layer assists in averaging heat distribution. Gold and/or silver are suitable as they are conductive and biocompatible. Optionally a further layer of parylene C or other insulation is added as the outer layer.

Possible arrangements for the electrical paths and temperature sensing means across the backing material are shown in FIGS. 3 and 4 of the accompanying drawings.

This form of heat transfer device can be fixed around a catheter at or near its distal end. Preferably the film is about 0.5–2.0 cm long, in order for it to remain within the main pulmonary artery trunk. The film could be fixed around the catheter starting at about 4–5 cm from the tip, and in the case of a PVC catheter body, the PVC film heat transfer device could be bonded by solvent.

Such a heat transfer device could be adapted to fit a catheter les than 7F diameter (2.3 mm). More preferably the heat transfer device can be incorporated in a catheter of 3-5F (1–1.67 mm) diameter. The heat transfer device should not increase the outer diameter of the catheter more than about 0.3F (0.1 mm).

Using the same technique, a similar film could be formed purely for temperature sensing. The temperature sensing material could be deposited on a backing film, followed by parylene (and gold) coatings. Such a temperature sensor could be positioned to 2–4 cm proximal to the heat transfer device. Optionally a further layer of parlyene C or other insulation is added as the outer layer.

According to another embodiment of the present invention, the heat transfer device is disposed onto the catheter wall by any known method of deposition, eg plasma deposition, printing, electroplating onto plastic, photo lithography etc. Application by printing uses eg conductive ink, or a conductive layer, with subsequently etching. This method of deposition can use any suitable resistive material. In addition, the temperature sensor material could be similarly applied.

According to a second aspect of the present invention, there is provided a catheter having a length of its outer wall formed wholly, substantially or partly from doped material able to act as a heat transfer device upon application of power therethrough.

This form of heat transfer device could be formed as an inherent part of the catheter wall, rather than as a separate addition of a heat transfer device to the catheter. The catheter wall is sufficiently doped with a resistive material or ingredient able to pass electrical current therethrough, without affecting its other properties. Any conductive material could be suitable, eg silver, gold.

According to a third aspect of the present invention, there is provided a catheter wall having one or more metal wires therethrough.

By locating the electrical connections within the catheter body wall, separate lumens for electrical connections to its distal end within the catheter interior are no longer required. These wires can also provide the catheter with the desired or required stiffness.

The wire(s) can be formed from any suitable metal, eg copper. Preferably, each wire is co-extruded within the catheter body.

More preferably, there are one or more sets of electrical wires in the catheter wall, each set having the required number of wires for the desired operations.

In one embodiment of the present invention, the catheter body has three sets of wires, each set comprising two wires. One set of wires is for a heating element, and the other two sets are for each of two temperature sensing elements located on or along the catheter wall, or one set for measuring ambient blood temperature, and the other set for measuring the temperature of the heat transfer device, or any other suitable combination of measurements.

The wire or wires inside the catheter wall should be easily exposable and thus connectable to the required electrical units to which they correspond. Any exposed wire could be covered by a suitable insulator such as vinyl adhesive, or urethane potting compound.

An example of this aspect of the present invention is shown in FIG. 2 of the accompanying drawings.

According to a preferred embodiment of the present invention, there is provided a catheter combining the first and third aspects described above.

One advantage of the use of one or more aspects of the present invention as described above is the ability to reduce the size of the catheter, more particularly for paediatric use. A catheter wherein the electrical wires required for the heat transfer device, etc are co-extruded within the catheter body, means that the catheter may only need a single distal lumen, (possibly 0.5–0.7 mm diameter) for solution infusion and pressure monitoring.

The novel apparatus and methods of the present invention could also be used in non-medical fields using heat transfer devices at or near the distal ends of elongate tubing to be located in remote locations. Such fields include aeronautics, any fluid flow analysis, food and drink processing and monitoring, water and sewerage management, chemical engineering, fuel supply to engines, etc.

The present invention is also particularly applicable to the paediatric catheter field.

Embodiments of the present invention are shown by way of example only in the accompanying diagrammatic drawings in which.

FIGS. 6a, b and c show a method of preparing a catheter having a heat transfer device.

The dimensions referred to in relation to accompanying diagrammatic drawings are illustrative only, and in no way limiting or essential.

Figure 1:
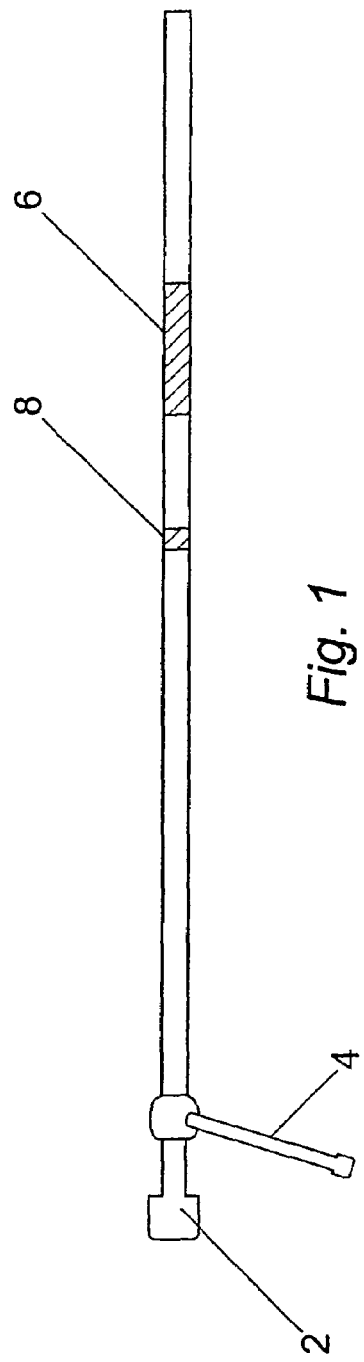
FIG. 1 is side view of a paediatric catheter.

Referring to the drawings, FIG. 1 shows the general form of a paediatric pulmonary artery catheter, which may be 70–100 cm long. At one end, such catheters generally have a connection 2, for example, to a TRUCCOM™, and a distal lumen 4. Such catheters are generally 3-5F size, i.e. approximately 1–1.67 mm diameter.

For all such catheters, the heat transfer device should preferably be in the range 0.5–2.0 cm long in order to remain within the main pulmonary artery trunk. The catheter body shore hardness should be about 45-55D for proper handling during insertion into patients. Use of softer materials may be possible, but may require the additional use of a wire to stiffen the catheter body allowing manoeuvrability during insertion.

In the versions of the present invention based on the layering or coating of the transfer device onto or into the catheter wall, the heat transfer device should not increase the outer diameter of the catheter more than 0.3F (0.1 mm).

FIG. 1 shows a schematic representation of a heat transfer device 6 according to the present invention 2 cm long, and located 4 cm from the end of the catheter. Thereafter is located a temperature sensor 8, approximately 0.3 cm long.

Figure 2:
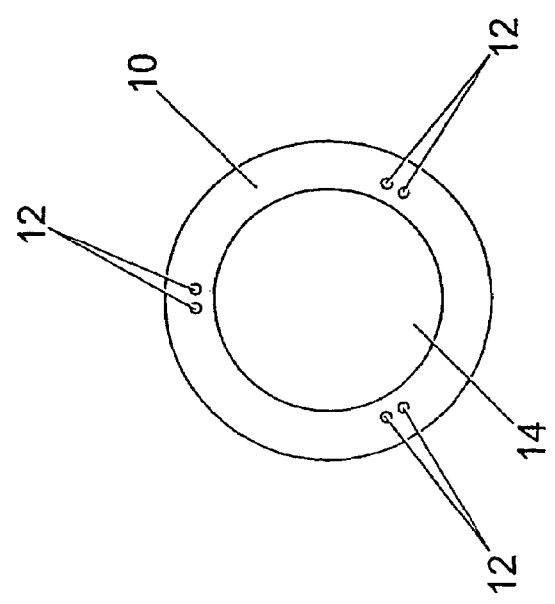
FIG. 2 is a radial cross-sectional view of a catheter wall having electrical wires located therein.

FIG. 2 is a cross-section of a catheter wall 10 wherein six copper wires 12 are co-extruded with the catheter body so as to be located in the catheter wall 10. Of the six wires, two are located for the heating element, and two for each of two temperature sensing elements (not shown). Thus, the catheter only has a single distal lumen 14, 0.5 mm diameter for solution infusion and pressure monitoring.

Figure 3:
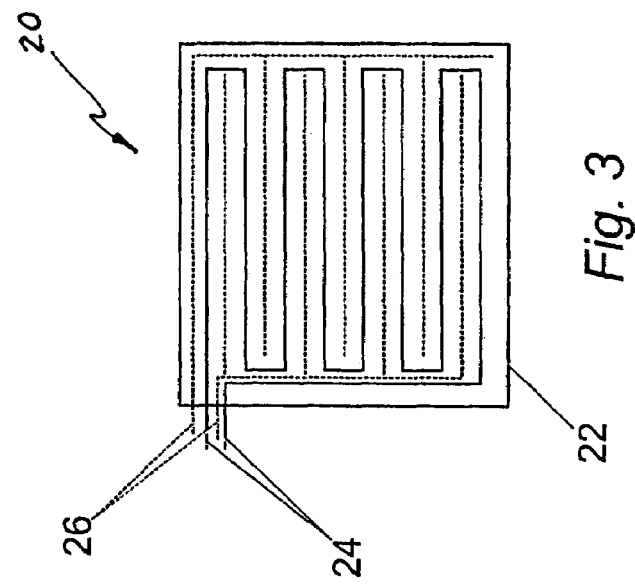
FIG. 3 is an example of a heat transfer device film for application around a catheter body.

FIG. 3 is an example of a flexible metal film heat transfer device 20 according to the present invention. The film consists of a thin high resistance metal film, e.g. of nickel, chromium or nickel-chromium, deposited on a PVC film 22, e.g. of 25–50 microns thick. The resistor wire 24 in FIG. 3 can be patterned using a photolithography mask. The device 20 includes temperature sensor leads 26.

Figure 4:
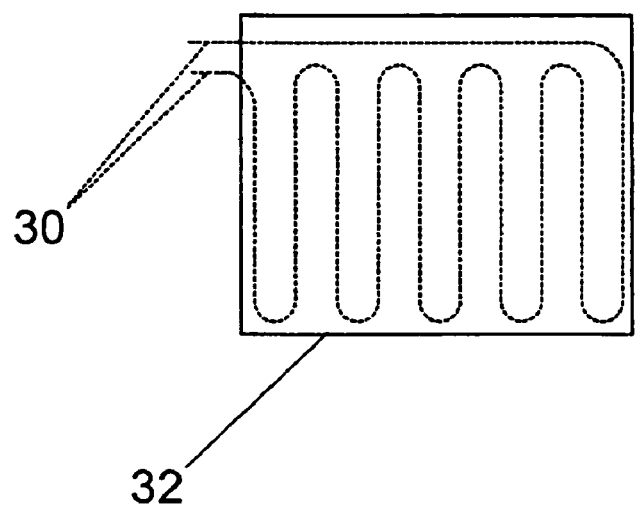
FIG. 4 is an example of a temperature sensor for application around a catheter body.

FIG. 4 shows a possible pattern for temperature sensor leads 30 on a similar PVC film 32 to act as a temperature sensor as shown in FIG. 1. It is similarly made to the device in FIG. 3, but only the temperature sensing material is deposited followed by Paralyene C and gold coatings.

Figure 5:
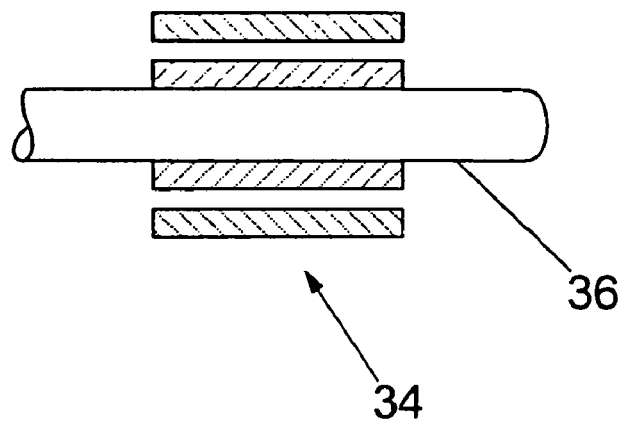
FIG. 5 is a longitudinal cross-sectional view of a catheter body having a heat transfer device therearound.

FIG. 5 shows a longitudinal cross-section of a catheter having a heat transfer device 34 based on that shown in FIG. 3. Around the catheter body 36 is a PVC film 0.05 mm thick. The resistor and temperature sensor leads are on the PVC film, which is then coated with a suitable insulator such as Parylene C, possibly of 0.005 mm thickness. The outer surface is coated with a silver or gold layer (suitably 5–10 microns thick).

As shown in FIGS. 6a–6c the overall heat transfer device 34 can be conjoined with the catheter body 36 using any suitable means such as a solvent. A temperature sensor 40 such as that shown in FIG. 4 is also conjoined with the catheter body 36, e.g. 2–4 cm proximal to the device 34. Thereafter, and as shown in FIGS. 6a–c, the wires 38 inside the catheter wall 36 are then exposed and the heat and temperature sensing wires are then connected and covered by a vinyl adhesive or another suitable insulator.

The invention claimed is:

1. A cardiac catheter having a distal end and a wall, the catheter comprising a heat transfer device located approximately at its distal end wherein the heat transfer device is engaged with a catheter wall and a temperature sensing element to measure native blood temperature, wherein the heat transfer device is a flexible film having at least one electrical resistor flow path and includes at least one temperature sensor included on or within the heat transfer device film to monitor the temperature of the electrical flow paths and thus the temperature of the overall heat transfer device wherein the heat transfer device is disposed directly onto the catheter wall.

2. A cardiac catheter as claimed in claim 1 wherein the heat transfer device is disposed onto the catheter wall by a deposition process.

3. A cardiac catheter as claimed in claim 2 wherein the deposition process is a plasma deposition process.

4. A cardiac catheter as claimed in claim 2 wherein the deposition process is a printing process.

5. A cardiac catheter as claimed in claim 4 wherein the printing process uses a conductive medium, with subsequent etching.

6. A cardiac catheter having a distal end and a wall, the catheter comprising a heat transfer device located approximately at its distal end wherein the heat transfer device is engaged with a catheter wall and a temperature sensing element to measure native blood temperature, wherein the heat transfer device is a flexible film having at least one electrical resistor flow path and includes at least one temperature sensor included on or within the heat transfer device film to monitor the temperature of the electrical flow paths and thus the temperature of the overall heat transfer device wherein the temperature sensor is also disposed onto the catheter wall by a deposition process.

7. A cardiac catheter a having a distal end and a wall, the catheter comprising a heat transfer device located approximately at its distal end wherein the heat transfer device is engaged with a catheter wall and a temperature sensing element to measure native blood temperature, wherein the heat transfer device is a flexible film having at least one electrical resistor flow path and includes at least one temperature sensor included on or within the heat transfer device film to monitor the temperature of the electrical flow paths and thus the temperature of the overall heat transfer device wherein at least one insulator layer is located over the electrical resistor flow path.

8. A cardiac catheter as claimed in claim 7 wherein at least one insulator layer is made from parylene C.

9. A cardiac catheter having a distal end and a wall the catheter comprising a heat transfer device located approximately at its distal end wherein the heat transfer device is engaged with a catheter wall and a temperature sensing element to measure native blood temperature, wherein the heat transfer device is a flexible film having at least one electrical resistor flow path and includes at least one temperature sensor included on or within the heat transfer device film to monitor the temperature of the electrical flow paths and thus the temperature of the overall heat transfer device wherein the heat transfer device comprises an outwardly located layer of material selected from a group consisting of silver or gold.

10. A cardiac catheter having a distal end and a wall, the catheter comprising a heat transfer device located approximately at its distal end wherein the heat transfer device is engaged with a catheter wall and a temperature sensing element to measure native blood temperature, wherein the heat transfer device is a flexible film having at least one electrical resistor flow path and includes at least one temperature sensor included on or within the heat transfer device film to monitor the temperature of the electrical flow paths and thus the temperature of the overall heat transfer device wherein a length of the outer wall of the catheter is at least partly formed from doped material able to act as a heat transfer device upon application of power therethrough.

11. A cardiac catheter as claimed in claim 10 wherein the doped material is selected from the group consisting of silver or gold.

12. A cardiac catheter having a distal end and a wall, the catheter comprising a heat transfer device located approximately at its distal end wherein the heat transfer device is engaged with a catheter wall and a temperature sensing element to measure native blood temperature, wherein the heat transfer device is a flexible film having at least one electrical resistor flow path and includes at least one temperature sensor included on or within the heat transfer device film to monitor the temperature of the electrical flow paths and thus the temperature of the overall heat transfer device wherein the catheter wall has at least one metal wire in at least a portion of the wall.

13. A cardiac catheter as claimed in claim 12 wherein at least one wire is copper.

14. A cardiac catheter as claimed in claim 12 wherein at least one wire is co-extruded within the catheter body.

15. A cardiac catheter as claimed in claim 12 wherein the catheter wall includes at least one set of wires.

16. A cardiac catheter as claimed in claim 15 wherein the catheter body has three sets of wires, each set comprising two wires.

17. A cardiac catheter as claimed in claim 12 wherein each wire inside the catheter wall is easily exposable.

* * * * *